US006858042B2

(12) United States Patent
Nadler et al.

(10) Patent No.: US 6,858,042 B2
(45) Date of Patent: Feb. 22, 2005

(54) PREPARATION FOR REPAIRING CARTILAGE DEFECTS OR CARTILAGE/BONE DEFECTS IN HUMAN OR ANIMAL JOINTS

(75) Inventors: Daniel Nadler, Winterthur (CH); Pedro Bittmann, Hettlingen (CH); Margarete Akens, Zürich (CH); Brigitte Rechenberg, Birmensdorf (CH); Jörg Auer, Lenzburg (CH)

(73) Assignee: Zimmer Orthobiologics, Inc., Austin, TX (US)

( * ) Notice: Subject to any disclaimer, the term of this patent is extended or adjusted under 35 U.S.C. 154(b) by 118 days.

(21) Appl. No.: 10/149,853

(22) PCT Filed: Dec. 12, 2000

(86) PCT No.: PCT/CH00/00659
§ 371 (c)(1),
(2), (4) Date: Oct. 17, 2002

(87) PCT Pub. No.: WO01/43667
PCT Pub. Date: Jun. 21, 2001

(65) Prior Publication Data
US 2003/0100947 A1 May 29, 2003

(30) Foreign Application Priority Data
Dec. 15, 1999 (CH) .............................................. 2296/99

(51) Int. Cl.[7] ................................................. A61F 2/02
(52) U.S. Cl. ................................ 623/11.11; 623/23.75; 424/423
(58) Field of Search ........................... 623/11.11, 18.11, 623/23.73, 23.72, 23.75, 16.11, 23.74; 606/80; 424/484, 423

(56) References Cited
U.S. PATENT DOCUMENTS
5,002,583 A * 3/1991 Pitaru et al. .............. 623/11.11

(List continued on next page.)

FOREIGN PATENT DOCUMENTS
DE 29 33 174 A 4/1980
(List continued on next page.)

OTHER PUBLICATIONS

WO 93/15694, Multi–Phase Bioerodible Implant/Carrier and Method of Manufacturing and Using Same, Publication Date Aug. 19, 1993.

(List continued on next page.)

Primary Examiner—Pedro Philogene
(74) Attorney, Agent, or Firm—Williams, Morgan & Amerson, P.C.

(57) ABSTRACT

Repairs of cartilage defects or of cartilage/bone defects in human or animal joints with the help of devices including a bone part (1), a cartilage layer (2) and a subchondral bone plate (4) or an imitation of such a plate in the transition region between the cartilage layer (2) and the bone part (1). After implantation, the bone part (4) is resorbed and is replaced by reparative tissue only after being essentially totally resorbed. In a critical phase of the healing process, a mechanically inferior cyst is located in the place of the implanted bone part (1). In order to prevent the cartilage layer (2) from sinking into the cyst space during this critical phase of the healing process the device has a top part (11) and a bottom part (12), wherein the top part (11) consists essentially of the cartilage layer (2) and the subchondral bone plate (4) and the bottom part (12) corresponds essentially to the bone part (1) and wherein the top part (11) parallel to the subchondral bone plate (4) has a larger diameter than the bottom part (12). After implantation in a suitable opening or bore (20), the cartilage layer (2) and the subchondral bone plate (4) are supported not only on the bone part (1) but also on native bone tissue having a loading capacity not changing during the healing process. Therefore, the implanted cartilage layer cannot sink during the healing process.

19 Claims, 6 Drawing Sheets

U.S. PATENT DOCUMENTS

| | | | |
|---|---|---|---|
| 5,152,791 A * | 10/1992 | Hakamatsuka et al. | 623/23.56 |
| 5,591,234 A | 1/1997 | Kirsch | |
| 5,632,747 A | 5/1997 | Scarborough et al. | |
| 5,718,707 A | 2/1998 | Mikhail | |
| 6,013,853 A * | 1/2000 | Athanasiou et al. | 424/423 |
| 6,179,871 B1 * | 1/2001 | Halpern | 623/11.11 |
| 6,251,143 B1 * | 6/2001 | Schwartz et al. | 623/23.72 |
| 6,626,945 B2 * | 9/2003 | Simon et al. | 623/17.19 |
| 6,626,950 B2 * | 9/2003 | Brown et al. | 623/23.72 |
| 2002/0013627 A1 * | 1/2002 | Geistlich et al. | 623/23.63 |
| 2003/0135209 A1 * | 7/2003 | Seedhom et al. | 606/60 |

FOREIGN PATENT DOCUMENTS

| | | |
|---|---|---|
| DE | 43 17 448 A | 11/1994 |
| DE | 195 03 504 A | 3/1996 |
| EP | 0 493 698 A | 7/1992 |
| EP | 0 768 332 A | 4/1997 |

OTHER PUBLICATIONS

WO 96/24310, Multi–Stage Collagen–Based Template or Implant for Use in the Repair of Cartilage Lesions, Publication Date Aug. 15, 1996.

WO 96/24302, Surgical Implantation of Cartilage Repair Unit, Publication Date Aug. 15, 1996.

WO 96/27333, Apparatus and Methods for Articular Cartilage Defect Repair, Publication Date Sep. 12, 1996.

WO 97/46665, Method for Making Cartilage and Implants, Publication Date Dec. 11, 1997.

WO 98/56317, Joint Prosthesis, Publication Date Dec. 17, 1998.

* cited by examiner

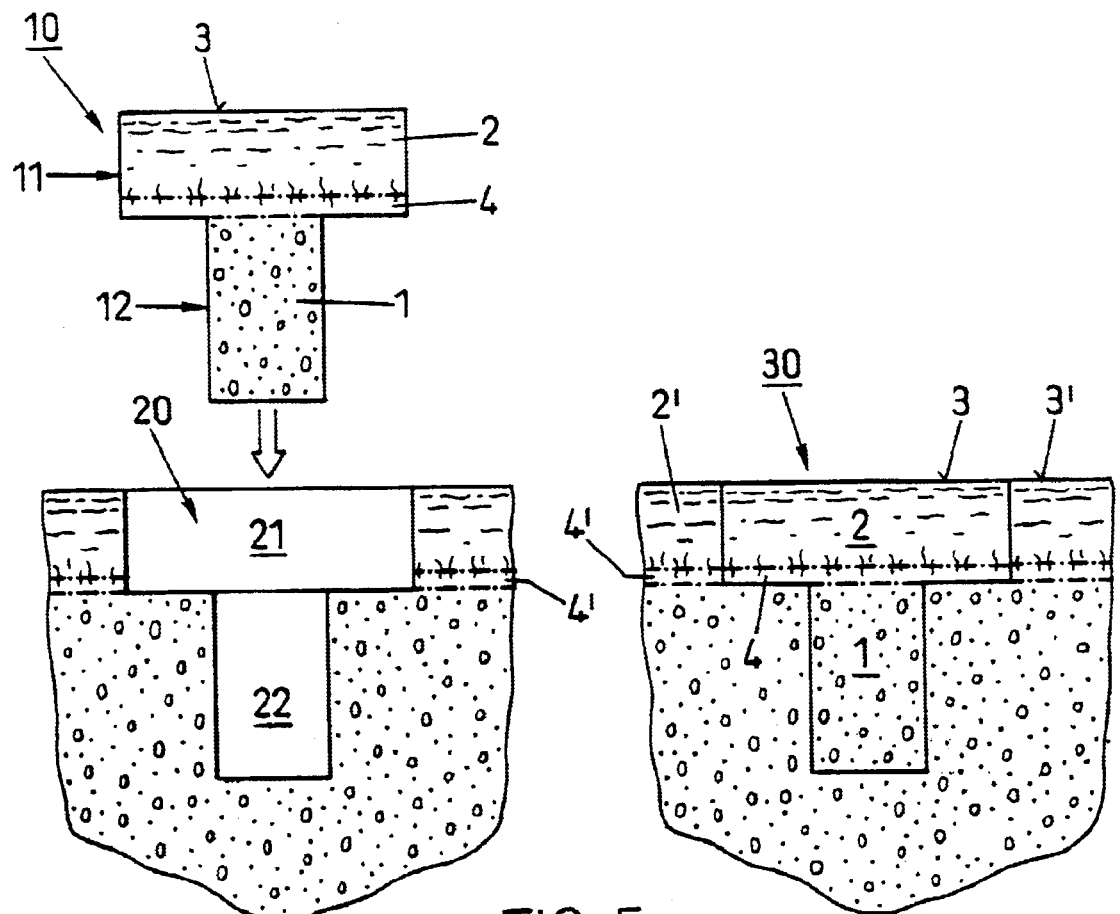
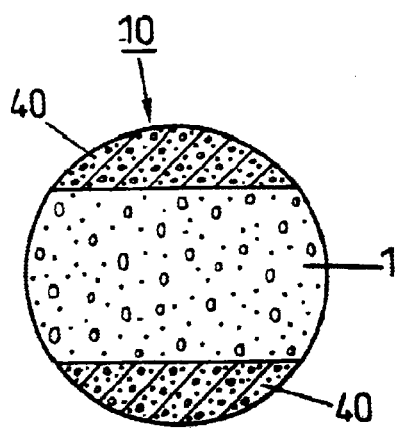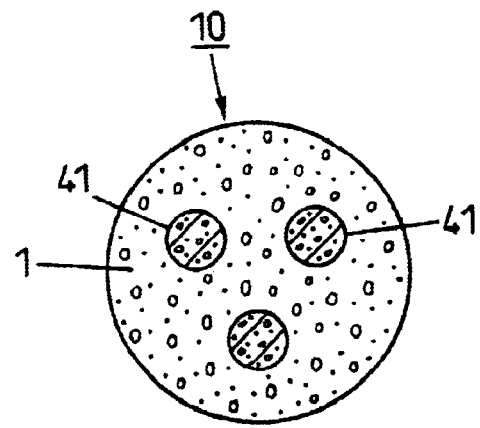
FIG. 6  FIG. 7

PREPARATION FOR REPAIRING CARTILAGE DEFECTS OR CARTILAGE/BONE DEFECTS IN HUMAN OR ANIMAL JOINTS

BACKGROUND OF THE INVENTION

1. Field of the Invention

The present invention lies in the field of medical technology and generally relates to a device for repairing cartilage defects and/or cartilage/bone defects in human or animal joints. More specifically, the device serves to repair defects in the cartilage layer, which in joints covers the bone surface, or of defects that concern this articular cartilage layer and also bone tissue lying thereunder.

2. Description of Related Art

Damage to articular cartilage by way of injuries or involution caused by aging or disease is particularly common in humans. Very often such damage also takes its toll on the bone tissue lying below the articular cartilage. The degree of damage to articular cartilage defects and/or cartilage/bone defects is determined with the help of the Outerbridge scale, with the following categories: superficial fraying (approx. 10% of all cases), cartilage fissure (approx. 28%), fissure down to the bone (approx. 41%), damage involving cartilage and bone (approx. 19%) and other damage such as osteochondritis dissecans and joint fracture (approx. 2% of all detected cases).

Vital cartilage tissue contains living cells by way of whose activity the specific intercellular cartilage matrix is built up during adolescence. However, it contains very little vascularization in the fully grown condition and, therefore, has a very limited regeneration capability. This means that cartilage defects or cartilage bone defects, in particular those defects concerning a relatively large cartilage surface, do not heal by themselves and therefore must be repaired by surgery (Mankin H J: The response of articular cartilage to mechanical injury, Journal of Bone and Joint Surgery (Am) 64A (1982) March: pages 460–466).

For repairing the named defects it is, for example, suggested to implant devices comprising the tissue to be repaired or a perform of this tissue. Such devices are cylindrical and comprise a cartilage layer on one end face. For implantation a pocket-hole shaped opening or bore is produced in the region of the defect to be repaired and the device is positioned in the bore such that the cartilage layer of the implant faces towards the outside. The bore, independently of the depth of the defect, extends into the healthy bone tissue. The device has a somewhat larger diameter than the bore and the same axial length. Therefore, after implantation there is a radial tension (press fit) between native tissue and the implanted device by way of which the implant is held in the bore. The cartilage surface of the implant is flush with the surrounding native cartilage surface. The devices have, according to the size of the defect, a diameter of 4 to 10 mm (e.g. 5.4 mm for the device and 5.3 mm for the bore) and lengths of approx. 10 to 20 mm.

For larger defects it is suggested to implant a plurality of such cylindrical devices in the defect region in a mosaic manner and to fill out the intermediate spaces between the implants with a suitable material.

The cylindrical devices are for example autologous (autotransplants). For the repair of an articular cartilage defect concerning a heavily loaded location of a joint, a suitable tissue piece is harvested, for example, from a less loaded location of the same joint and is transplanted into a bore created at the defect location using a hollow drill (Hangody L et al.: Mosaicplasty for the treatment of articular cartilage defects: application in clinical practice. Orthopedics 1998 Jul., 21(7):751–6).

The cylindrical devices may also originate from a suitable donor (homologous transplants). Also known are suitable heterologue implants or xenotransplants which before implantation are suitably treated, e.g. photo-oxidized (as described in the publication EP-0768332 of Sulzer Innotec), for preventing immune-reaction after implantation or for minimizing such immuno-reaction (immunological deactivation). Such implants are, for example, removed from shoulder joints of slaughtered cattle and have the advantage of being available in much larger numbers than autologous or homologous transplants and of causing no secondary defects on harvesting, which secondary defects must be repaired and lead to new difficulties.

In the publication WO-97/46665 (Sulzer Orthopedics) a suitable device is described of which the bone part consists of bone replacement material and the end-face cartilage layer is grown onto it in vitro from autologous chondrocytes.

In all mentioned devices being made from natural tissue there is a natural connection or coalescence between the end-face cartilage layer and the bone part and there is an outermost bone region (subchondral bone plate) in which the bone tissue is more compact than in other bone regions. The mentioned, partly artificial implants also show the coalescence of cartilage layer and bone part and the artificial bone part is advantageously equipped with a more compact, that is to say less porous, outer layer which serves the cartilage layer as an underlay.

An important function of the subchondral bone plate or an artificial imitation thereof is evidently the prevention of vascularisation of the cartilage layer proceeding from the bone tissue, which would lead to ossification of the cartilage. In addition the subchondral bone plate having a higher density than the inner bone tissue represents a region of higher mechanical strength.

With the devices as mentioned above it is attempted to achieve the following targets:

The bone part of the device is to allow solid anchoring of the implant by way of a press fit, in a manner such that the implant requires no further fastening means interfering with healthy cartilage regions.

The coalescence of cartilage layer and bone part in the device is to give the implant stability so that the cartilage layer cannot be detached and removed from the defect location, even if the joint is not immobilized after implantation.

The cartilage layer of the device Is to have a mechanical strength and elasticity such that the repair location may be fully loaded directly after implantation.

The cartilage layer is to form a zone in which conditions suitable for the implanted cells or for cells migrating into it after implantation prevail, such that the cell can produce or maintain a fully functional cartilage tissue. This is also to be supported by the subchondral bone plate which separates the cartilage layer from the bone part and which helps to prevent vascularisation proceeding from the bone part.

The bone part is to represent a zone in which conditions suitable for the implanted cells or for cells migrating into it after implantation prevail, such that they can produce or maintain a fully functional bone tissue.

New trials in which artificially produced defects in joints of sheep have been repaired with auto-transplants, homo-transplants or with hetero-transplants (from cattle tissue) in the previously mentioned manner, show that the healing process after implantation does not proceed as expected.

In particular, it has been shown that the bone part of the implants is not integrated in the native tissue or replaced gradually by new reparative tissue, but that the bone part of the implant undergoes a transformation process with essentially three successive phases. In a first step bone osteoclastic cells (osteoclasts) are stimulated and the implanted bone starts to be resorbed. This first phase is already clearly visible six to eight weeks after implantation. A hollow space (cyst) then arises in the implant and is filled with connective tissue. This second phase reaches a climax after approximately six weeks. In the third and last phase bone-forming cells (osteoblasts) are attracted which convert the connective tissue to bone. This conversion process is concluded after about twelve months. Then the newly created bone structure is so well adapted that the original border between the implant and the surrounding bone tissue can hardly be perceived anymore.

Due to the described, three-phase transformation process comprising a middle phase in which the cartilage layer of the implant is not carried by the bone part capable to do so but by a mechanically inferior cyst, there exists a high risk that the cartilage layer is pressed into this cyst where it can neither fulfill its mechanical nor its biological function and from where it cannot be displaced during the following phases of the healing process. This risk significantly reduces the chances of healing success. Healing with a badly positioned cartilage layer causes negative after-effects.

It is surprising that the trials show the cyst formation at the location of the bone part of an implant in a middle phase of the healing process not only for homologous and heterologous implants, but in particular also for auto-transplants. The initial resorption of the implanted bone tissue does not therefore appear to be an immuno-reaction in which implanted vital material is recognized as foreign and is therefore resorbed. It would appear that it is rather a reaction to implanted, dead material. This means that by cutting off the natural blood supply on harvesting the implant even when harvesting it from viable tissue and even when it is implanted directly after harvesting, the bone tissue loses its viability. In any case, the bone part of the implant is resorbed and is rebuilt only after substantially complete resorption.

SUMMARY OF THE INVENTION

It is an object of the invention to provide a device for repairing cartilage defects or cartilage/bone defects in human or animal joints, which device prevents the above described risk of an implanted cartilage layer to sink into the region of the native bone tissue. The device according to the invention allows production and implantation in a manner equally simple as for known devices comprising a bone part and a cartilage layer calescent with the bone part.

The device according to the invention that serves for repairing cartilage defects or cartilage/bone defects in human or animal joints, is based on the finding that the subchondral bone plate is evidently present essentially unchanged when the bone part is completely or to a great extent replaced by connective tissue in the middle critical phase of the above described healing process. This is probably attributed to the fact that the subchondral bone plate, on account of its higher density, is resorbed significantly more slowly than the inner regions of the bone part. Since this subchondral bone plate is mechanically sufficiently stable, sinking of the cartilage layer grown thereon into a cyst underneath is prevented when the subchondral bone plate is supported not only by implanted bone material but in addition by material with different resorption properties such that during the critical healing phase it remains non-displaceable. When the subchondral bone plate of the implant is resorbed after the critical phase, that is to say at a point in time in which the loading capability of the inner implant region is restored again, this will not greatly influence the healing process.

Improved support of the implanted device during the critical healing phase can be realized in essentially two ways.

On the one hand the implant may be formed such that the cartilage layer and the subchondral bone plate of the device have a larger cross section than the bone part. Such a device is implanted into a two stage bore such that the subchondral bone plate of the device is not only supported on the bone part of the implant but also on healthy bone tissue next to the bore set up for repair.

On the other hand the bone part of the device may be equipped with columns having a reduced resorbability. These columns extend axially through the bone part up to the subchondral bone plate. The resorbability of the columns relative to the resorbability of the bone part regions between the columns may be reduced by way of a suitable chemical treatment or by way of producing axial bores in the bone part of the device and filling these with an artificial material more resistant to resorption.

BRIEF DESCRIPTION OF THE DRAWINGS

These and further features of the invention will be apparent with reference to the following description and drawings, wherein:

FIG. 5 shows a schema of the repair of a cartilage defect with the help of a preferred embodiment of the device according to the invention (section along the axis of the device or the bore);

FIGS. 6 and 7 show two further exemplary embodiments of the device according to the invention, in cross section; and, FIGS. 8 and 9 show sections through a cartilage defect (FIG. 8) and through a cartilage/bone defect (FIG. 9), both repaired in a mosaic manner with a plurality of inventive devices according to FIG. 5.

DETAILED DESCRIPTION OF THE PREFERRED EMBODIMENTS

Figure 1:
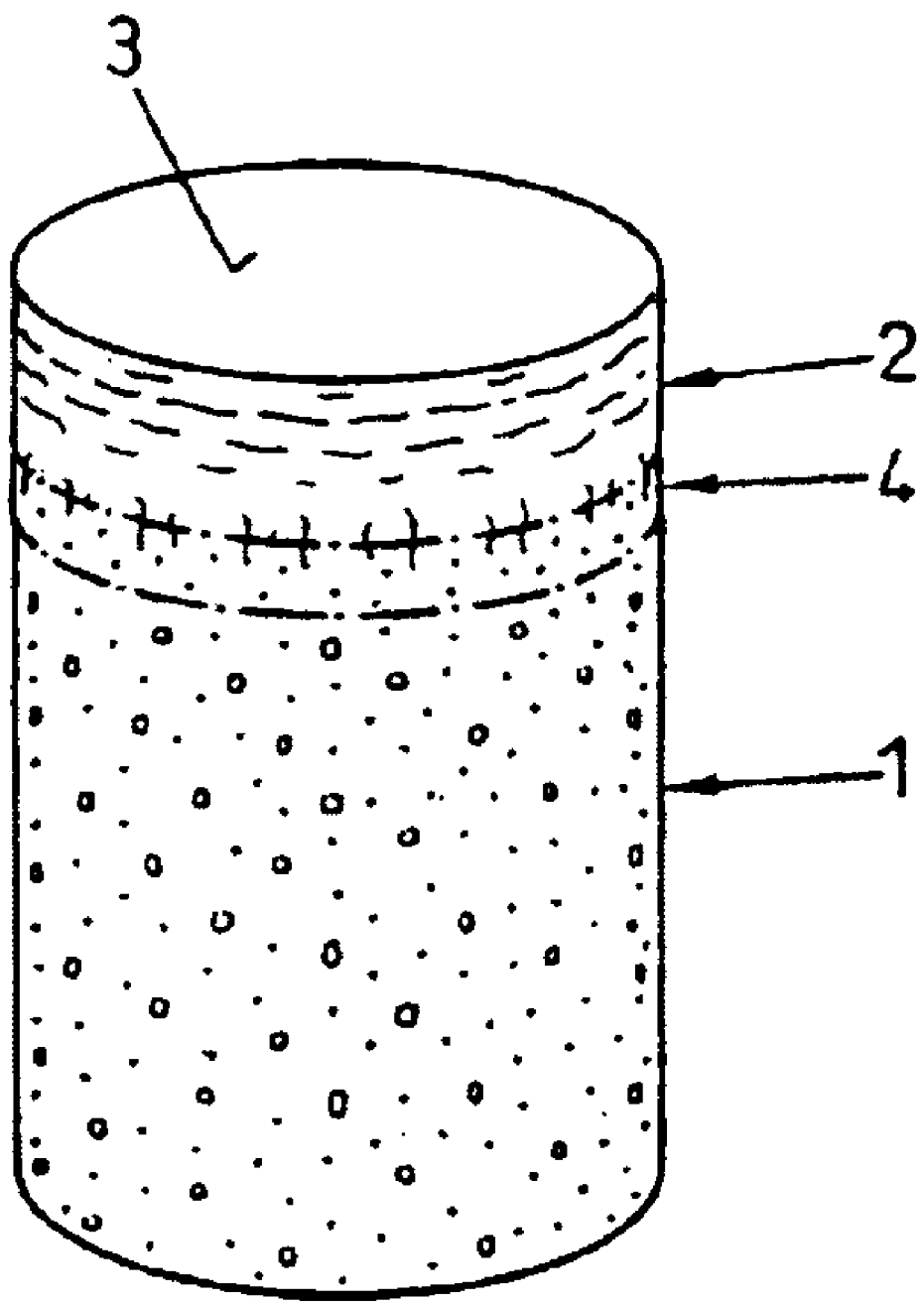
FIG. 1 shows a known cylindrical device for repairing cartilage defects or cartilage/bone defects in human or animal joints.

FIG. 1 shows a device as used according to the state of the art for repairing cartilage defects or cartilage/bone defects in human or animal joints. The device is cylindrical, advantageously with a circular cross section, and comprises a bone part 1 and cartilage layer 2 grown on one end face onto the bone part 1. The cartilage layer 2 forms a cartilage surface 3. Between the bone part 1 and the cartilage layer 2 there extends a subchondral bone plate 4. The transitions from the bone part 1 to the subchondral bone plate 4 and from the subchondral bone plate 4 to the cartilage layer 2 are not visible as lines, as is shown in FIG. 1 in a simplified manner, but they are natural, rather continuous transitions.

As already mentioned a device as shown in FIG. 1, is harvested from advantageously vital tissue using a hollow drill and is implanted if possible immediately after harvesting (auto-transplants and homo-transplants), or it is removed from joints of slaughtered animals (e.g. from shoulder joints of slaughtered cattle) and before implantation is subjected to a treatment for immunological deactivation.

Figure 2:
FIGS. 2 to 4 show tissue sections through cartilage/bone defects in a sheep's joint being repaired with a device according to FIG. 1, at various points in time after the implantation.
Figure 3:
Figure 4:

FIGS. 2 to 4 illustrate the trials with implants according to FIG. 1 in sheep's joints which have already been discussed further above and they further illustrate the risk connected with such implants. The drawings show tissue sections through repair locations parallel to the axis of the implant, which in the enlarged drawings projects from the cartilage surface (top side of the Fig.) about 7 cm into the bone tissue. FIGS. 2 and 3 show implant sites six months after implantation with cyst-like cavities in the bone tissue. FIG. 2 shows a case in which the cartilage layer is still positioned at its original location, in FIG. 3 it has sunk into the cyst space.

As is evident from FIGS. 2 and 3, in the critical time period in which at the location of the implanted bone part there is a cyst-like cavity, the subchondral bone plate of the implant is substantially unchanged. This finding is attributed to the higher density of the subchondral bone plate relative to the inner bone tissue and therefore a reduced resorbability. The subchondral bone plate of the implant has evidently different resorption properties than have inner regions of the bone part.

The trials were carried out with auto-transplants and with hetero-transplants. For seven treated animals the repair locations were examined after six months and in ten cases (five animals) cartilage layers were found to be displaced into the cyst cavity, in four cases (two animals) the cartilage layers had remained in place. In none of the cases the cartilage layer was lost into the joint space.

The results of the trials show that evidently adhesion between the cyst and the implanted cartilage layer or the subchondral bone plate respectively is sufficient for preventing removal of the cartilage layer from the repair location, but that the loading capability of the cyst is not sufficient for preventing the cartilage layer from being displaced towards the inside.

FIG. 4 shows a similar repair location twelve months after implantation. An unevenness in the cartilage surface caused by the sinking-in of the implanted cartilage layer is clearly visible. In the series of trials repair locations on seven treated animals were examined after twelve months and in two cases unevennesses in the cartilage surface as shown in FIG. 4 were found. In the remaining cases the cartilage surface in the repair region was even.

FIG. 5 shows a preferred embodiment of the device according to the invention for repairing cartilage or cartilage/bone defects in human or animal joints. It shows the device 10, the opening or bore 20 to be set up for implantation of the device, and the device inserted in the opening, the implanted device 30 (section along the axis of the device 10 or of the opening 20).

The device 10 has in the same manner as the device of FIG. 1 a bone part 1, and on one end face of this, a cartilage layer 2 forming a cartilage surface 3. In the transition region between the bone part 1 and the cartilage layer 2 there is a subchondral bone plate 4. The device has a top part 11 with a larger cross section and a bottom part 12 with a smaller cross section. The top part 11 comprises essentially the cartilage layer 1 and the subchondral bone plate 4, the bottom part 12 essentially corresponds to the bone part 1. The bottom part 12 has advantageously (but not necessarily) the shape of a circular cylinder or steep angle truncated circular cone and the top part 11 projects on all sides beyond the bone part 1 and is for example likewise circularly cylindrical.

Auto-transplants and transplants of living donors have advantageously cylindrical top parts since such devices should cause as small as possible harvesting sites. Devices produced from the tissue of slaughtered animals (advantageously cattle or pigs) may without causing problems have head parts with any shape of cartilage surface. This is so due to the easy availability of the material allowing production of wastage. But also in this case it is advantageous to form the bottom part in a manner such that the opening to be made for implantation can be created with a simple tool, for example with a drill.

A device 10 with circular cross section at least in the foot region is for example manufactured from a suitable cylindrical device in that the bone part is accordingly machined. This machining may be carried out with a tool In which the cylindrical device is positioned and in which blades are activated to reduce the cross section of the device 10 to a predetermined extent at a predetermined or adjustable distance from the cartilage surface.

The opening or bore 20 which is to be created in a defect region for implanting the device 10 has an outer region 21 adapted to the top part 11 of the device 10 and having a depth down to the region of the native subchondral bone plate 4', and an inner region 22 adapted to the bottom part of the device, whose depth is adapted to the shape of the defect to be repaired and to the length of the device to be implanted. The dimensions of the device 10 and of the bore 20 are to allow for a press fit in the region of the top part as well as in the region of the bottom part.

A bore 20 as shown in FIG. 5 is for example created with a tool comprising a blade with a circular cutting edge and two drills or hollow drills movable relative to the cutting edge in an axially limited manner. The tool is positioned on the defect location and the blade is pressed down to the subchondral bone plate. Then the outer region 21 is drilled out with the first drill, which may be moved beyond the cutting edge of the blade by the thickness of the subchondral bone plate, and whose diameter corresponds essentially to the inner diameter of the blade. Afterwards the inner region 22 is drilled out using the second drill, wherein the drilling depth relative to the cutting edge or relative to the end position of the first drill may be adjusted.

FIG. 5 shows on the right hand side the implanted device 30, that is to say the device 10 implanted in the bore 20. The implanted device 30 comprises a cartilage surface 3 flush with the native cartilage surface 3' and a subchondral bone plate 4 roughly flush with the native subchondral bone plate 4'. The subchondral bone plate 4 of the implant is evidently supported on the one hand on the bone part 1 of the implant and on the other hand on native bone tissue directly below the native, subchondral bone plate 4' or in its region. For achieving a press fit for the head region 1 of the implant, it is advantageous to dimension the outer region 21 of the bore with a depth such that the subchondral bone plate 4 of the implant is not only radially supported on native cartilage tissue 3' but also on native bone tissue (subchondral bone plate 4'), as this is shown in FIG. 5.

For implanting a device in a bore, as shown by FIG. 5, a tool is used. The tool comprises, for example, a sleeve and a plunger axially movable in the sleeve. The sleeve has an inner cross section that corresponds to the cross section of the top part of the device to be implanted. The plunger advantageously has a cross section roughly equal to the top part; it is longer than the sleeve and has a channel that begins on the end face of the plunger and is connectable to a suction conduit in the region of the other end of the plunger.

For implantation, the end face of the plunger with the channel opening is pushed into the sleeve and using the suction force, a device to be implanted is drawn into the sleeve. Then the sleeve together with the plunger and the device suctioned thereon is positioned over the prepared bore and the device is pressed into the bore with the help of the plunger and where appropriate using a hammer.

It has been shown that resorption of the bone part of an implanted device also affects regions of the native bone tissue bordering the implant. For this reason it is recommended to dimension the protrusion of the top part to about 1 to 2 mm (e.g., bone part with a diameter of approximately 3 mm, top part with a diameter of 5 to 6 mm).

FIGS. 6 and 7 show two further exemplary embodiments of the device according to the invention. These are not based on the idea of supporting the subchondral bone plate of the device on native bone tissue as is shown in FIG. 5, but rather on the idea of establishing in the bone part at least one column having a resorbability different from the resorbability of the rest of the bone material in the bone part 1 such that at the point in time in which the remaining bone tissue of the bone part is resorbed, the columns bear the subchondral bone plate and the cartilage layer grown onto it and, therefore, prevent the cartilage from sinking into the cyst region.

FIGS. 6 and 7 are cross sections through bone parts 1 of devices according to the invention. These devices are, for example, cylindrical and in the bone part have axially extending columns consisting of a material that is resorbed more slowly than the bone material of the regions between the columns. The columns are, for example, arranged on the surface of the bone part (surface columns 40 in FIG. 6) and are produced by a suitable treatment of the bone material, or they are located in the inside of the bone part (inner columns 41 in FIG. 7) and are produced by creating bores and filling the bores with a suitable material. In both cases, the columns extend up to at least the subchondral bone plate.

For local reduction of the resorbability of bone material, a treatment with biphosphonate may be used ("Biophosphonates in Bone Disease" Herbert Fleisch, the Parthenon Publishing Group, New York and London 1995). As a resorbable material for filling bores for example a hydroxy apatite ceramic material may be used.

Figure 8:
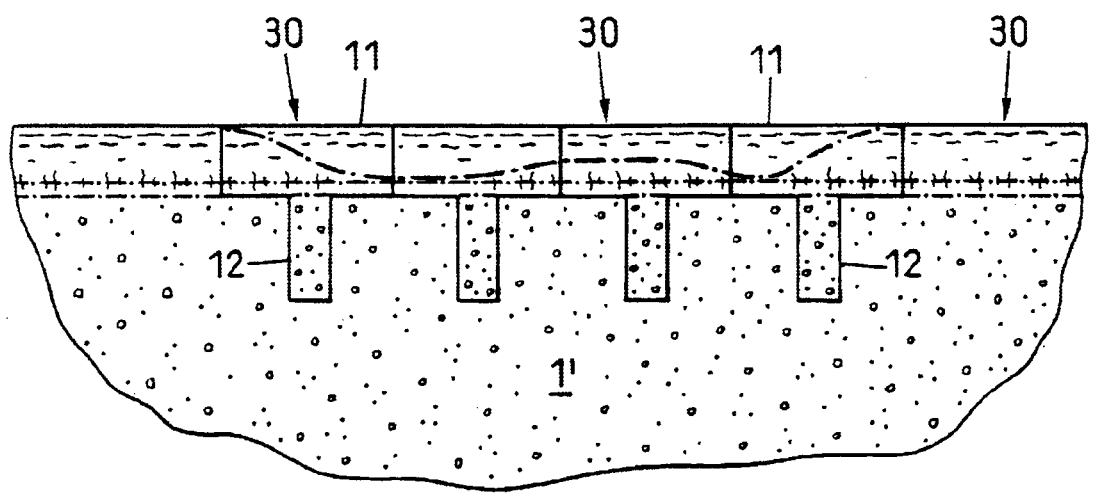
Figure 9:
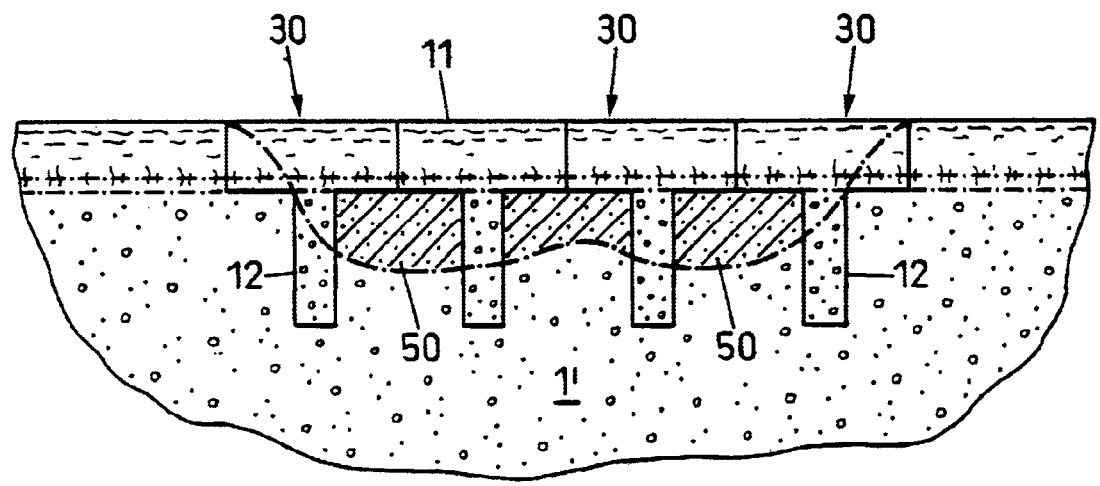

FIGS. 8 and 9 show a cartilage defect (FIG. 8) and a cartilage/bone defect (FIG. 9) with dimensions of the type such that they cannot be repaired with a single implant. The defects are indicated with dot-dashed lines. The repair consists of a mosaic-like arrangement of devices according to the invention, as shown in FIG. 5.

As mentioned above, it is possible also to use implants according to the state of the art (FIG. 1) for such mosaic-like arrangements for repairing larger defects. The cylindrical devices are implanted as close as possible next to one another, wherein on the one hand there will be gaps in the cartilage layer and on the other hand the regions of native bone tissue between the bone parts of the implants will be very narrow. It has been shown that the chances of healing of such repairs are better in edge regions than in middle regions. One may presume that this is due, on the one hand, to the deficient compactness of the freshly created cartilage layer and, on the other hand, to the deficient repair ability of the greatly reduced native bone tissue between the implants.

FIG. 8 shows that the implants 30 with the top parts 11 also in a mosaic repair allow supporting of the cartilage layer and the subchondral bone plate of the implants on native bone tissue 1' and thereby counteract a sinking of the cartilage layer in a critical healing phase. It is also evident that the regions of native bone tissue 1' between the bottom parts 12 of the implants are wider than the case would be with cylindrical implants. This means that the healing chances are improved in contrast to the state of the art. It is also evident that the cartilage surface may be formed essentially without interruption over the complete defect region if the shape of the top parts is accordingly selected (e.g. square, rectangular, triangular, or hexagonal).

FIG. 9 shows a cartilage/bone defect (indicated with a dot/dashed line) that has been repaired with a plurality of devices according to FIG. 5. The bottom parts 12 of the implants 30 extend into healthy bone tissue 1'. Locations 50 where bone material is missing or damaged bone material has been removed are filled out with a suitable material (for example tricalcium phosphate or hydraulic bone cement). This material is to be selected such that it is resorbed either before or after the bottom parts 12 of the implants 30 and so that, in the critical phase of the healing process in which the bone parts of the implants are resorbed and not yet replaced, it can support the cartilage layers and prevent them from sinking. Advantageously the filling material has a mechanical strength sufficient for being drilled straight after being filled into the defect.

The additional advantages described for the repair according to FIG. 8 apply also to the repair according to FIG. 9.

What is claimed is:

1. A device (10) for repairing cartilage defects or cartilage/bone defects in human or animal joints, said device comprising a bone part (11), a cartilage layer (2) grown onto the bone part (1) and forming a cartilage surface (3), and a subchondral bone plate (4) or an imitation of a such a bone plate in a transition region between the bone part (1) and the cartilage layer (2), said device being implantable into an opening or a bore (20) set up in a defective region such that the bone part is adapted to be ordered in the healthy bone tissue and the cartilage surface (3) is flush with a native cartilage surface (3'), wherein for supporting the subchondral bone plate (4) and the cartilage layer (2) of the implanted device on at least two materials with differing resorbabilities, a cross-section of the bone part (1) is smaller than a cross section of the subchondral bone plate (4) and the cartilage layer (2) or the bone part has column regions (40, 41) that extend to the subchondral bone plate (4) and have a resorbability different from a resorbability of the regions between the column regions.

2. The device according to claim 1, further comprising a top part (11) and a bottom part (12), wherein the top part (11) substantially comprises the cartilage layer (2) and the subchondral bone plate (4), and the bottom part (12) substantially corresponds to the bone part and wherein the subchondral bone plate (4) is larger than a cross section parallel to the subchondral bone plate through the bottom part (12) such that the subchondral bone plate (4) of the implanted device (30) is supported on native bone tissue.

3. The device according to claim 2, wherein the top part (11) and the bottom part (12) are coaxial circular cylinders.

4. The device according to claim 2, wherein the bottom part (12) is a circular cylinder and the top part (11) has a square, rectangular, triangular or hexagonal cartilage surface (3).

5. The device according to claim 1, wherein the column regions (40, 41) extend perpendicular to the subchondral bone plate (4) through the bone part (1) up to the subchondral bone plate (4), and wherein the column regions (40, 41) and regions between the column regions have different resorbabilities.

6. The device according to claim 5, wherein the device is essentially cylindrical and the cartilage layer (3) is arranged on one of its end faces.

7. The device according to claim 5, wherein a resorption behavior of the column regions (40) is altered with respect to a resorption behavior of the regions between the column regions by way of chemical treatment.

8. The device according to claim 7, wherein the column regions (40) consist of bone issue treated with biphosphonate.

9. The device according to claim 1, wherein the column regions (41) consist of a bone replacement material filled into corresponding axial bores.

10. The device according to claim 1, wherein said device is made of autologous tissue.

11. The device according to claim 1, wherein said device is made of homologous or heterologous, immunologically deactivated issue.

12. The device according to claim 11, wherein said device is made of tissue that is immunologically deactivated by way of photo-oxidation.

13. The device according to claim 11, wherein said device consists of tissue removed from slaughtered animals.

14. The device according to claim 13, wherein the tissue is removed from cattle or pig's joints.

15. A method for repairing cartilage defects or cartilage/bone defects in human or animal joints using a device (10) according to claim 2, comprising the steps of producing in the defect region an opening or bore (20) extending into healthy bone material and implanting the device (10) in the opening or bore, wherein the opening (20) comprises an outer region (21) and an inner region (22), a cross section of the outer region (21) is larger than a cross section of the inner region (22) and wherein the opening (20) is adapted, relative to the device (10), such that the device is implantable with a press fit and the cartilage surface (3) of the implanted device (30) is flush with the native cartilage surface (3').

16. The method according to claim 15, wherein a transition between the outer region (21) and the inner region (22) lies directly below the native subchondral bone plate (4').

17. The method according to claim 15, wherein the opening (20) is produced by drilling.

18. The method according to claim 15, wherein, for repairing larger defects, a plurality of devices are implanted in a mosaic-like manner, wherein positions for openings or bores (2) and the shape and size of top parts (11) of the devices (10) are coordinated to one another such that a cartilage surface (3, 3') essentially without interruption is achieved.

19. The method according to claim 18, wherein missing bone material between the openings is replaced with a bone replacement material having a resorbability that is different from the resorbability of the bone parts (1) of the devices (10).

* * * * *

UNITED STATES PATENT AND TRADEMARK OFFICE
CERTIFICATE OF CORRECTION

PATENT NO. : 6,858,042 B2
DATED : February 22, 2005
INVENTOR(S) : Daniel Nadler et al.

It is certified that error appears in the above-identified patent and that said Letters Patent is hereby corrected as shown below:

Column 8,
Line 42, change "to be ordered" to -- to be anchored --.

Column 9,
Line 24, change "issue" to -- tissue --.

Signed and Sealed this

Seventeenth Day of May, 2005

JON W. DUDAS
*Director of the United States Patent and Trademark Office*